United States Patent [19]

Grimm

[11] Patent Number: 4,585,525

[45] Date of Patent: Apr. 29, 1986

[54] PURIFYING TRIMETHYLPHENOL BY AZEOTROPIC DISTILLATION

[75] Inventor: Richard C. Grimm, South Charleston, W. Va.

[73] Assignee: Union Carbide Corporation, Danbury, Conn.

[21] Appl. No.: 536,971

[22] Filed: Sep. 29, 1983

[51] Int. Cl.$^4$ .............................................. B01D 3/38
[52] U.S. Cl. ...................................... 203/62; 568/810
[58] Field of Search .................. 252/DIG. 9; 203/57, 203/62; 568/774, 779, 796, 810

[56] References Cited

U.S. PATENT DOCUMENTS 2,360,655 10/1944 Deansly ................................ 203/64

Primary Examiner—Frank Sever
Attorney, Agent, or Firm—G. L. Coon

[57] ABSTRACT

A method of removing alicyclic ketones and chlorotrimethylphenol from a mixture of alicyclic ketones, chlorotrimethylphenol and trimethylphenol by azeotropically distilling such a mixture in the presence of a glycol or a dialkyl sulfoxide.

4 Claims, No Drawings

PURIFYING TRIMETHYLPHENOL BY AZEOTROPIC DISTILLATION

FIELD OF THE INVENTION

This invention relates to the purification of a crude reaction product mixture by azeotropic distillation. More particularly, this invention relates to azeotropic compositions of an alicyclic ketone or chlorotrimethylphenol and an azeotropic agent and the use of such compositions in an azeotropic distillation.

BACKGROUND OF THE INVENTION

A mixture of 2,3,5- and 3,4,5-trimethylphenol is synthesized from the chlorination of isophorone as intermediates in the production of the pesticidal compounds 2,3,5- and 3,4,5-trimethylphenyl methylcarbamates. The reaction product mixture from the chlorination of isophorone contains the desired isomers of trimethylphenol as well as from about 5% to about 10% by weight of unreacted isophorone, and about 14% to about 23% by weight of by-products such as chlorotrimethylphenol, tars and high-boiling residue. The tars and high-boiling residue can be removed by distilling the mixture. However, the major remaining impurities, isophorone and chlorotrimethylphenol, cannot be satisfactorily removed in a conventional fractional distillation because the boiling point of chlorotrimethylphenol is very close to the boiling points of the trimethylphenol isomers and isophorone forms a maximum-boiling azeotrope with the trimethylphenol isomers that is about 5% by weight isophorone. As a result, it is not possible to obtain trimethylphenol by conventional fractional distillation of a purity greater than about 96% by weight that is acceptable for the production of 2,3,5- and 3,4,5-trimethylphenyl methylcarbamates.

U.S. Pat. Nos. 3,392,090 and 3,830,708 disclose the purification of phenolic compounds by azeotropic distillation with the formation of 2,6-dimethylphenol/-glycol, acylic ketone/glycol and mixed hydrocarbon/-glycol azeotropes. U.S. Pat. Nos. 3,827,974 and 3,331,755 disclose the purification of phenolic compounds by extractive distillation. None of these references, however, disclose the separation of alicyclic ketones or chlorotrimethylphenol from trimethylphenol by azeotropic distillation.

SUMMARY OF THE INVENTION

This invention is directed to the formation of azeotropic compositions in an azeotropic distillation to remove the alicyclic ketones and chlorotrimethylphenol from a mixture of trimethylphenol, alicyclic ketones and chlorotrimethylphenol. The alicyclic ketones that can be separated from trimethylphenol by the practice of this invention have the following structural formula:

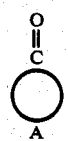

wherein A is a 5, 6, or 7 membered alkylene or alkenylene radical substituted with up to four alkyl groups having not more than four carbon atoms each. The alkylene or alkenylene radicals are divalent hydrocarbon radicals which are saturated or ethylenically unsaturated, respectively. When A is —CH=C(CH$_3$)—CH$_2$—C(CH$_3$)$_2$—CH$_2$—, the alicyclic ketone is isophorone.

I have found that glycols containing not more than four carbon atoms, dialkyl sulfoxides containing not more than four carbon atoms or mixtures thereof form minimum-boiling azeotropes with alicyclic ketones and chlorotrimethylphenol which can be employed to effect the desired separation. Because these azeotropes have boiling points substantially below the boiling point of the maximum-boiling alicyclic ketone/trimethylphenol azeotropes, alicyclic ketones and chlorotrimethylphenol can be separated from trimethylphenol by fractionally distilling them in the presence of the azeotropic agent.

DETAILED DESCRIPTION OF THE INVENTION

The trimethylphenol product mixtures prepared from the chlorination of isophorone in the production of trimethylphenyl methylcarbamates typically contain 5–10% by weight isophorone, 3–6% by weight chlorotrimethylphenol, 10–15% high-boiling residues, and 1–2% each of at least two unidentified mid-boiling compounds. To have optimum utility in further syntheses, this trimethylphenol must be purified to at least about 96% by weight trimethylphenol. The data in the table below, Table I, illustrate the difficulty of obtaining such purity by a conventional fractional distillation of the mixture because of the closeness of the chlorotrimethylphenol boiling point to those of the trimethylphenol isomers and the formation of an isophorone/trimethylphenol azeotrope.

TABLE I

| Component | Boiling Point at 120 torr (°C.) |
|---|---|
| 2,3,5-trimethylphenol | 171 |
| 3,4,5-trimethylphenol | 185 |
| 2-chloro-trimethylphenol | 193 |
| isophorone | 147 |
| isophorone/2,3,5-trimethylphenol* azeotrope | 181 |

*4–5% isophorone/96–95% 2,3,5-trimethylphenol

A set of azeotropic agents will form minimum-boiling azeotropic compositions with isophorone or chlorotrimethylphenol that can be separated from the isomers of trimethylphenol by fractional distillation. These azeotropic agents are ethylene glycol, 1,2-propylene glycol, 1,3-propylene glycol, 1,2-butylene glycol, 1,3-butylene glycol, 1,4-butylene glycol, dimethyl sulfoxide, diethyl sulfoxide and mixtures thereof. The preferred azeotropic agents are the glycols that have a hydroxyl group at each end of the carbon chain, in particular, ethylene glycol. They all are characterized by their ability to form minimum-boiling azeotropes with alicyclic ketones and chlorotrimethylphenol.

The azeotropic distillation can be conducted over a wide range of pressures, as measured at the head of the distillation column (head pressure). The general range of suitable head pressures is from about 10 torr to slightly above atmospheric pressure, with the proviso that the azeotropic agent selected boil within about 15° C., and preferably within about 10° C., of the boiling point of the alicyclic ketone at the selected head pressure. This proviso ensures that the selected azeotropic agent will form an effective azeotrope with the alicyclic ketone at the selected head pressure.

Although isophorone and ethylene glycol are miscible, it has been found that a distillate of ethylene glycol/isophorone azeotrope separates into two liquid phases. The top phase is rich in isophorone and chlorotrimethylphenol and at least two unknown compounds which may be ketals formed by the reaction of isophorone with ethylene glycol. The bottom phase is ethylene glycol with a minor amount of isophorone such that the bottom layer can be recycled to reduce the total amount of glycol needed in the system to remove a given amount of isophorone and chlorotrimethylphenol impurities.

The preferred method of azeotropically distilling a crude trimethylphenol mixture includes the use of a conventional two-column distillation train. A crude mixture of trimethylphenol, isophorone and chlorotrimethylphenol is fed to the midpoint of a distillation column containing about 18 to 22 theoretical stages operating at a head pressure between about 25 to 200 torr. Azeotropic agent is fed into the column near the midpoint or with the feed to insure that sufficient azeotroping agent is present in the trays below the trimethylphenol mixture feedpoint to form the relatively more volatile azeotroping agent/isophorone or chlorotrimethylphenol azeotropes. The isophorone and chlorotrimethylphenol azeotropes are removed overhead to a decanter where impure isophorone and chlorotrimethylphenol concentrate in top layer which is removed. The azeotropic agent concentrates in a bottom layer which can be returned as make-up or reflux to the first column.

The trimethylphenol isomers, along with high-boiling residue and any excess azeotropic agent are removed as bottoms from the first column and fed to a point about 2 or 3 theoretical stages below the head of a second distillation column containing about 5 to 9 theoretical stages. The azeotropic agent, if any, is removed overhead from the second column and is discarded or recycled back to the first column. The purified trimethylphenol isomers are removed as vapor about one stage above the bottom of the second column and the tars and high-boiling residue are removed as bottoms.

EXAMPLE

A semi-batch azeotropic distillation of a representative mixture of crude trimethylphenol, was conducted in a single column laboratory distillation apparatus. A 1000 gm charge of ethylene glycol was charged to the kettle of a laboratory distillation column containing 20 Oldershaw 28 mm diameter sieve trays of approximately 65% efficiency. The head pressure was reduced to 100 torr and the ethylene glycol was heated to total reflux. The following crude product mixture as outlined below:

| 3,4,5-trimethylphenol; | 1752.3 gm; | 59.4% |
| 2,3,5-trimethylphenol; | 252.5 gm; | 8.56% |
| isophorone; | 295 gm; | 10.0% |
| chlorothimethylphenol; | 123.9 gm; | 4.2% |
| high-boiling residue; | 424.8 gm; | 14.4% |
| unidentified volatiles; | 99.4 gm; | 3.37% |
| total; | 2948 gm; | 99.9% | was fed to the midpoint of the column. The feed line was heated to about 90° to maintain the feed in a liquid state.

The overhead make was then taken in a first overhead fraction at a reflux-to-make ratio of 15 from the column head to a decanter. The head pressure was maintained at 100 torr by a controlled bleed through a line from the decanter to a cold trap and mechanical pump. The condensed distillate formed two liquid phases. The top and bottom layers were taken separately for analysis. The composition of this first fraction was as follows:

|  | Top Layer |  | Bottom Layer |  |
| --- | --- | --- | --- | --- |
| 3,4,5-trimethylphenol | 11.3 gm | 3.5% | 1.1 gm | 0.1% |
| 2,3,5-trimethylphenol | 16.0 gm | 5.0% | 6.9 gm | 1.0% |
| isophorone | 174.1 gm | 54.4% | 42.2 gm | 6.0% |
| chlorotrimethylphenol | 22.5 gm | 7.0% | 4.0 gm | 0.6% |
| ethylene glycol | 58.9 gm | 18.4% | 595.5 gm | 84.3% |
| unidentified volatiles | 33.3 gm | 10.4% | 64.6 gm | 6.6% |
| water | 2.1 gm | 0.7% | 32.0 gm | 4.5% |
| total | 320 gm | 100% | 706 gm | 100% |

After about 19 hours of operation, when about 65% of the 1000 gm ethylene glycol charge had been collected, the feed was discontinued and a second fraction was taken overhead at a reflux-to-make ratio of 15 until the temperature at the midpoint of the column rose from 135° C. to 175° C. and the head temperature rose from 125° C. to 135° C. (at 110-120 torr). The composition of the second fraction was as follows:

| 3,4,5-trimethylphenol; | 0.8 gm; | 0.2% |
| 2,3,5-trimethylphenol; | 39.7 gm; | 9.4% |
| isophorone; | 42.0 gm; | 10.0% |
| chlorotrimethylphenol; | 16.3 gm; | 3.8% |
| ethylene glycol; | 296.2 gm; | 70.0% |
| unidentified volatiles; | 27.4 gm; | 4.8% |
| water; | 18.2 gm; | 4.3% |
| total; | 424 gm; | 100% |

The column was then maintained at total reflux to keep trimethylphenol from freezing in the head of the column and to remove the residual glycol from the lower trays of the column. The refined trimethylphenol product was then removed as vapor at a reflux-to-vapor make ratio of 4 in a third cut from just above the kettle. The composition of the third fraction was as set forth below:

| 3,4,5-trimethylphenol; | 1430.9 gm; | 89.2% |
| 2,3,5-trimethylphenol; | 134.4 gm; | 8.4% |
| isophorone; | 16.6 gm; | 1.0% |
| chlorotrimethylphenol; | 22.3 gm; | 1.4% |
| total; | 1600 gm; | 100% |

The kettle residue of 976 gm contained 10.7 gm of 3,4,5-trimethylphenol (1.1%) and 965.3 gm of otherwise unidentified high-boiling residue (98.9%).

A comparison of the trimethylphenol isomer yield in the third fraction of (1430.9 gm+134.4 gm=) 1665.3 gm with the charge of trimethylphenol of (1752.3 gm+252.5 gm=) 2004.8 gm shows that approximately 80% of the trimethylphenol isomers charged in a crude mixture can be recovered at a combined purity of (89.2%+8.4%=) 97.6%. This value, well within practical requirements for the synthesis of trimethylphenyl methylcarbamates, could not be achieved in a conventional fractional distillation without the use of an azeotropic agent and the formation of isophorone and chlorotrimethylphenol azeotropic compositions in accordance with this invention.

I claim:

1. A method of removing isophorone and chlorotrimethylphenol from a mixture of trimethylphenol, isophorone and chlorotrimethylphenol comprised of distilling said mixture in the presence of an azeotropic agent selected from ethylene glycol, 1,2-propylene glycol, 1,3-propylene glycol, 1,2-butylene glycol, 1,3-butylene glycol, 1,4-butylene glycol, dimethyl sulfoxide, diethyl sulfoxide and mixtures thereof.

2. The method of claim 1 wherein the glycol selected is ethylene glycol.

3. The method of claim 1 wherein the glycol selected is propylene glycol.

4. The method of claim 1 wherein the dialkyl sulfoxide selected is dimethylsulfoxide.